United States Patent
Lv et al.

(10) Patent No.: US 10,500,147 B2
(45) Date of Patent: *Dec. 10, 2019

(54) TOOTHPASTE WITH ALGINATE BASED RHEOLOGY MODIFIER

(71) Applicant: COLGATE-PALMOLIVE COMPANY, New York, NY (US)

(72) Inventors: Xiaojing Lv, Guangzhou (CN); Manying Shi, Guangzhou (CN); Zhuoxing Zhang, Guangzhou (CN)

(73) Assignee: Colgate-Palmolive Company, New York, NY (US)

( * ) Notice: Subject to any disclaimer, the term of this patent is extended or adjusted under 35 U.S.C. 154(b) by 279 days.

This patent is subject to a terminal disclaimer.

(21) Appl. No.: 15/113,933

(22) PCT Filed: Jan. 24, 2014

(86) PCT No.: PCT/CN2014/071312
§ 371 (c)(1),
(2) Date: Jul. 25, 2016

(87) PCT Pub. No.: WO2015/109511
PCT Pub. Date: Jul. 30, 2015

(65) Prior Publication Data
US 2016/0346185 A1    Dec. 1, 2016

(51) Int. Cl.
| | | |
|---|---|---|
| *A61K 8/00* | (2006.01) |
| *A61K 8/25* | (2006.01) |
| *A61K 8/86* | (2006.01) |
| *A61Q 11/00* | (2006.01) |
| *A61K 8/60* | (2006.01) |
| *A61K 8/19* | (2006.01) |
| *A61Q 17/00* | (2006.01) |
| *A61K 8/73* | (2006.01) |
| *A61K 8/34* | (2006.01) |
| *A61K 8/46* | (2006.01) |

(52) U.S. Cl.
CPC ............ *A61K 8/60* (2013.01); *A61K 8/19* (2013.01); *A61K 8/345* (2013.01); *A61K 8/463* (2013.01); *A61K 8/731* (2013.01); *A61K 8/733* (2013.01); *A61Q 11/00* (2013.01); *A61Q 17/005* (2013.01); *A61K 2800/28* (2013.01); *A61K 2800/34* (2013.01); *A61K 2800/48* (2013.01); *A61K 2800/59* (2013.01)

(58) Field of Classification Search
CPC .......... A61K 8/733; A61K 8/25; A61K 8/345; A61K 8/86; A61K 2800/30; A61K 2800/48; A61K 2800/92; A61Q 11/00
See application file for complete search history.

(56) References Cited

U.S. PATENT DOCUMENTS

| | | | |
|---|---|---|---|
| 4,401,648 A | 8/1983 | Piechota, Jr. | |
| 4,765,984 A | 8/1988 | Vellekoop et al. | |
| 5,366,742 A | 11/1994 | Tuason, Jr. et al. | |
| 5,482,932 A * | 1/1996 | Thompson ........... | A61L 26/0023 424/443 |
| 6,335,001 B1 | 1/2002 | Palkrishnan et al. | |
| 9,713,586 B2 | 7/2017 | Shi et al. | |
| 2006/0275223 A1 * | 12/2006 | Burr ....................... | A61K 8/345 424/49 |
| 2006/0280713 A1 | 12/2006 | Malessa | |
| 2012/0315228 A1 | 12/2012 | Deng et al. | |

FOREIGN PATENT DOCUMENTS

| | | |
|---|---|---|
| CN | 102219938 | 10/2011 |
| EP | 1453488 B1 | 10/2009 |
| JP | 2009-120552 | 6/2009 |
| WO | WO 2012/152054 | 11/2012 |
| WO | WO 2015039277 | * 3/2015 |

OTHER PUBLICATIONS

International Search Report and the Written Opinion of the International Searching Authority issued in International Patent Application PCT/CN2013/071321 dated Oct. 22, 2014.
International Preliminary Report on Patentability in International Patent Application PCT/CN2013/071321 dated Jul. 26, 2016.
Wei Yi et al.: "The Application of Rheology in Preparing of Toothpaste Formula", Journal of Guangxi University of Technology, vol. 9, No. 1, Mar. 31, 1988 (Mar. 31, 1988), pp. 77 4.1.
Wei Yi et al.: "Study on the Toothpaste Rheological Properties for Formulation of Recipe", China Surfactant Detergent & Cosmetics, Jun. 30, 1999 (Jun. 30, 1999), pp. P10.
Wei et al., 1999, "Study of Toothpaste Rheological Properties for Formulating of Recipe," Daily Chemical Industry 3:8-10 Abstract only in English.
Llaneras, 2000, "Marine Freshwater & Products Handbook," Technomic Publishing Co. Inc., pp. 537-538.
Kao, 2012, "Fresh Mint Flavoured Medicated Toothpaste," Mintel GNPD AN: 1775851.

* cited by examiner

*Primary Examiner* — Lezah Roberts

(57) ABSTRACT

The present invention provides oral care compositions, and in particular toothpaste compositions comprising a calcium salt abrasive and a novel alginate-based binder and rheology modifier, together with methods of use and manufacture thereof.

16 Claims, 1 Drawing Sheet

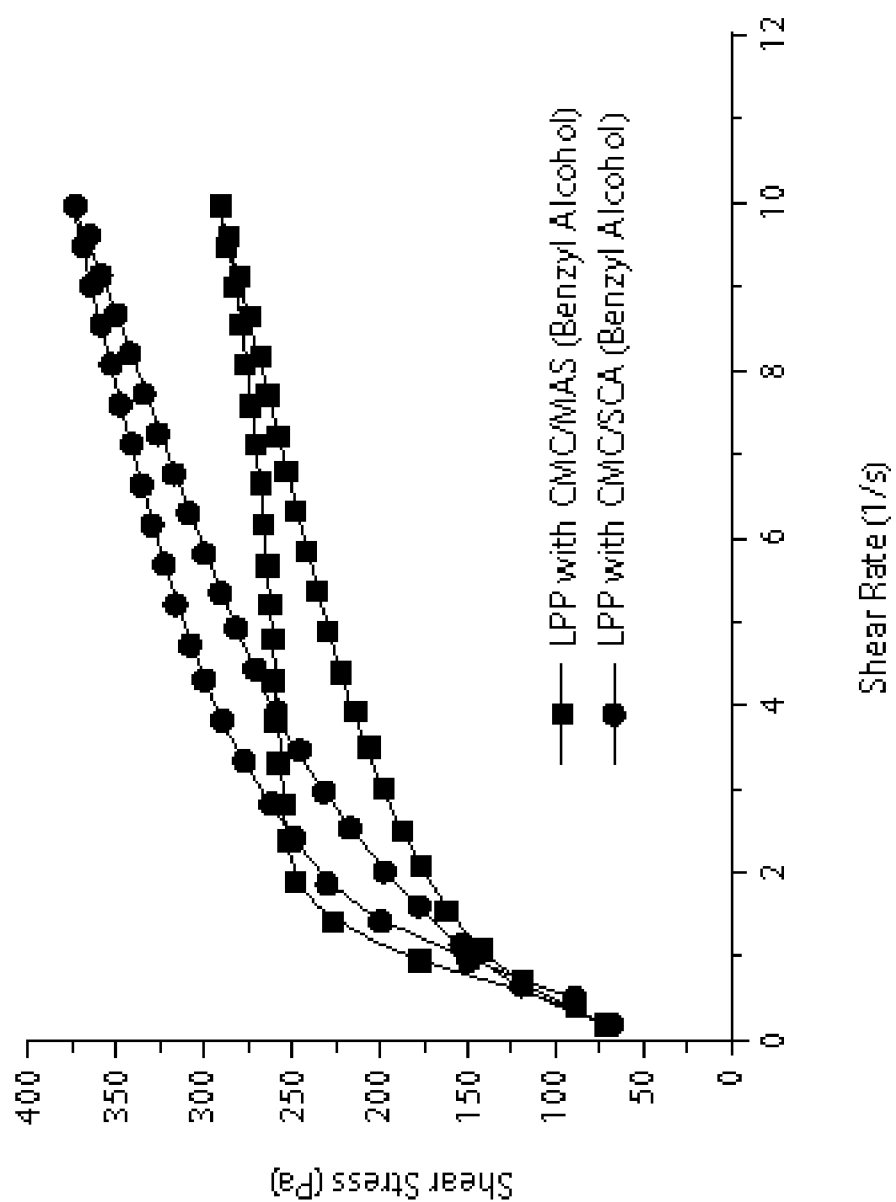

TOOTHPASTE WITH ALGINATE BASED RHEOLOGY MODIFIER

FIELD

The present invention relates to oral care compositions, and in particular toothpaste compositions that contain a particular alginate-based binder and rheology modifier.

BACKGROUND

Gum disease affects a significant number of people worldwide, and is a leading cause of tooth loss. Gum disease usually begins with gingivitis, in which bacteria in dental plaque build up, causing the gums to become inflamed. Dental plaque is a soft deposit which forms on teeth and is comprised of an accumulation of bacteria and bacterial by-products. Plaque adheres tenaciously at the points of irregularity or discontinuity, e.g., on rough calculus surfaces, at the gum line and the like. A wide variety of formulations have been developed to incorporate color and other ingredients into stripes, to improve the appearance of the toothpaste and thus increase patient compliance. However, formulating striped toothpaste presents challenges in terms of preserving the required rheological, viscosity and foaming and properties while incorporating active ingredients in effective amounts. Striped toothpaste products typically include two materials. A first material, usually white, is at the crimp end of the toothpaste tube and makes up most of its bulk. A second material, having a different color, e.g., red, is located at the other end of the tube, and there is a channeling means, such as a thin perforated pipe to the nozzle of the toothpaste tube, which allows the two materials to be extruded together, the second material forming a stripe on the first material. Typically, the two materials are not in separate compartments, and they should be sufficiently viscous that they will not mix, but not so viscous that it becomes difficult to dispense the toothpaste. The two materials may have substantially the same composition, except for the coloring, or may have different compositions.

Calcium carbonate abrasives, for example, chalk, are commonly used as an abrasive in toothpaste, but require a suitable binder to provide a paste formulation having good viscosity and mouthfeel. Magnesium aluminum silicate may be used as a binder in such formulations, but also may be costly. Alginates, such as sodium alginate and calcium alginate, have been suggested as alternative binders, but sodium alginate tends to result in low viscosity, drippy formulations, while calcium alginate tends to confer a stringy texture, so neither are ideal for this purpose.

Accordingly, there exists a need for novel compositions that are suitable for use in striped toothpastes. This invention is directed to these, as well, as other, important ends.

SUMMARY

Unless otherwise indicated, the terms "%" or "percent" when used in connection with an ingredient of the toothpaste compositions of the invention is intended to refer to the percent by weight of the indicated ingredient in the toothpaste composition.

Unless otherwise indicated, the terms "%" or "percent" when used in connection with an ingredient of the toothpaste compositions of the invention is intended to refer to the percent by weight of the indicated ingredient in the toothpaste composition.

In some embodiments, the present invention provides a toothpaste composition, for example a striped toothpaste, comprising an abrasive, e.g., calcium carbonate, and a binder, wherein the binder comprises "sodium calcium alginate" (SCA). "Sodium calcium alginate" refers to a complex salt of alginic acid (a high molecular weight anionic polysaccharide, bearing numerous carboxy groups), wherein some of the carboxy group on the molecule form salts with sodium, some with calcium. It is quite distinct in its chemical structure and physical properties from sodium alginate, calcium alginate or mixtures of these two. In particular embodiments, the ratio by weight of sodium to calcium in the SCA is from 7:1 to 4:1, e.g., 6:1 to 5:1; for example about 84:16. In some embodiments, the toothpaste is free of magnesium aluminum silicate.

In some embodiments, the sodium calcium alginate binder is present in the toothpaste in an amount of from 0.09% to 1.1%; or 0.1%, of the toothpaste by weight.

In further embodiments, the toothpaste comprises an abrasive that includes or is composed of calcium carbonate, e.g., natural calcium carbonate, in an amount of from 25% to 60%; 30% to 55%; 35% to 50%; 40% to 45%; or about 40%, 41%, 42%, 43%, 44% or 45% of the toothpaste by weight.

In some embodiments, the toothpaste further comprises carboxymethylcellulose in an amount of up to 5%, or from, 0.1% to 3%; or from 0.1% to 2%, or from 0.5% to 1.5%, or 1% of the toothpaste by weight.

In some embodiments, the toothpaste comprises a humectant which includes or is composed of one or more polyols, e.g., sorbitol, in an amount of from 16% to 26%, or from 12% to 24%; or about 21% of the toothpaste by weight.

In some embodiments, the toothpaste further comprises thickener silica in an amount of from 1% to 3%; or about 2%, of the toothpaste by weight.

In some embodiments, the toothpaste further includes one or more detergents or surfactants. In some embodiments, the toothpaste further includes sodium lauryl sulfate (SLS). In some embodiments, the sodium lauryl sulfate is present in an amount of from 1% to 3%, for example 2%, of the toothpaste by weight.

In some embodiments, the toothpaste further includes a fluoride source, for example and without limitation monofluorophosphate (MFP), sodium fluoride, or stannous fluoride. In some embodiments, the fluoride source is present in an amount of from 0.5% to 1.0%; or 0.7% to 0.8%; of the toothpaste by weight.

In some preferred embodiments, the binder system comprises sodium alginate and calcium alginate in a ratio of from 7:1 to 4:1, e.g., 6:1 to 5:1; for example about 84:16; the sodium calcium alginate binder is present in the toothpaste in an amount of 0.1%, of the toothpaste by weight; the abrasive compises natural calcium carbonate, in an amount of from 40% to 45%; or 41% to 43%, or 42%, of the toothpaste by weight; and the toothpaste further comprises carboxymethylcellulose in an amount of from 0.1% to 2%, or 1%, of the toothpaste by weight. In some further embodiments, the binder system further comprises from 16% to 26% sorbitol; from 1% to 3% sodium lauryl sulfate; from 0.5% to 2% of a fluoride source; and thickener silica in an amount of 2% of the toothpaste by weight.

In some embodiments, the toothpaste further comprises one or more adjuvants selected from sweetening agents flavoring agents and coloring agents. In some embodiments, the flavoring agent is present in an amount of from 0.5% to 2.0%; or 1% of the toothpaste by weight.

In some embodiments, the toothpaste is a striped toothpaste.

The present invention also provides methods for reducing bacterial growth in an oral cavity compising contacting the oral cavity with a toothpaste of the invention.

BRIEF DESCRIPTION OF THE FIGURE

The FIGURE shows a graph of results from a rheology study conducted on the 0.10% SCA binder.

DETAILED DESCRIPTION

It has been discovered in accordance with the present invention that the use of a sodium calcium alginate binder having a defined ratio of sodium alginate to calcium alginate as disclosed herein in a toothpaste composition, and paiticularly in a toothpaste composition containing calcium carbonate, for example natural calcium carbonate (NCC), provides thickening, binding, foaming and rheological properties uniquely suitable for toothpaste compositions, and in particular, striped toothpaste compositions. While not wishing to be bound by any particular theory, it is believed that these properties result from calcium ion cross-linking of alginate to form a three-dimensional network. The novel binder system disclosed herein can replace magnesium aluminum silicate in toothpaste compositions.

Thus, in some embodiments, the present invention provides a toothpaste composition, for example a striped toothpaste, comprising a binder system and an abrasive, wherein the binder system comprises sodium calcium alginate, wherein the sodium calcium alginate has a sodium:calcium ratio of from 7:1 to 4:1, e.g., 6:1 to 5:1, e.g., about 84:16.

The sodium calcium alginate binder of the present invention imparts several properties, e.g., viscosity, mouthfeel, and foaming properties, that are equivalent to or superior to magnesium aluminum silicate. Accordingly, the sodium calcium alginate binder of the present invention can replace magnesium aluminum silicate in toothpaste compositions, and particularly in toothpaste compositions containing calcium carbonate, e.g. natural calcium carbonate.

Preferably, the sodium calcium alginate binder of the present invention is present in the toothpaste composition in an amount of from 0.09% to 1.1%; or 0.1%, of the toothpaste by weight.

The toothpaste compositions further comprise an abrasive comprising from calcium salts, e.g. calcium carbonate and/or a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate. In a particular embodiment, the abrasive includes or is composed of calcium carbonate. Any of the calcium carbonates known to be useful in the dentifrice art are suitable for inclusion in the toothpaste compositions of the invention. In some embodiments, the calcium carbonate is natural calcium carbonate (NCC). The amount of calcium carbonate in the toothpaste compositions of the invention is for example from 25% to 60%; 30% to 55%; 35% to 50%; 40% to 45%; or 40%, 41%, 42%, 43%, 44% or 45% of the toothpaste by weight.

The toothpaste compositions of the invention can further include one or more additional binding agents, for example polymers including polyethylene glycols, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 33,000 to about 1,000,000, most preferably about 300,000 to about 800,000. In some preferred embodiments, the toothpaste compositions of the invention include an additional binding agents (i.e., in addition to the sodium calcium alginate binder disclosed herein) derived from cellulose, preferably a cellulose ether, for example carboxymethylcellulose (CMC), e.g. having a medium to high degree of polymerization, e.g. 1000 to 3000, for example about 2000, e.g., in sodium salt form, e.g., CMC 2000s, in an amount effective to provide the desired viscosity and stability, e.g., in an amount of up to 5%, or from, 0.1% to 3%; or from 0.1% to 2%, or from 0.5% to 1.5%, or 1% of the toothpaste by weight.

The toothpaste compositions of the invention further include humectant, i.e. one or more humectants. Examples of suitable humectants include polyhydric alcohols (polyols) such as propylene glycol, glycerin, sorbitol, xylitol or low molecular weight polyethyleneglycols (PEGs). In various embodiments, humectants can prevent hardening of paste or gel compositions upon exposure to air, and also function as sweeteners. In some embodiments, the humectant system consists primarily or solely of sorbitol, e.g., in an amount of from 16% to 26%, or from 18% to 24%; or about 21% of the toothpaste by weight. However, the presence of other humectants still providing satisfactory toothpaste properties is also contemplated.

In some embodiments, the toothpaste compositions of the invention further include one or more thickeners (i.e., thickening agents), which aid in obtaining the proper viscosity of the composition. Generally, the thickener is present in the composition in an amount of from 1% to 5%. Examples of thickening agents include, without limitation, the binding agents described above, which also modify viscosity, for example carboxyvinyl polymers, carrageenans (also known as Irish moss and more particularly iota-carrageenan), cellulosic polymers such as hydroxyethylcellulose, carboxymethylcellulose (carmellose) and salts thereof (e.g., carmellose sodium), natural gums such as karaya, xanthan, gum arabic and tragacanth, colloidal magnesium aluminum silicate, colloidal silica, and mixtures thereof. One preferred thickener is thickener silica, for example in an amount of from 1% to 3%, for example 2%, by weight of the toothpaste.

The toothpaste compositions of the invention can further include one or more detergents or surfactants. Surfactants useful for the present invention include, without limitation: anionic, nonionic, and amphoteric surfactants. Surfactants may be used, for example, to provide enhanced stability of the formulation, to help in cleaning the oral cavity surfaces through detergency, and to increase foaming of the composition upon agitation, e.g., during brushing. Suitable anionic surfactants include, for example, water-soluble salts of $C_{8-20}$ alkyl sulfates, sulfonated monoglycerides of $C_{8-20}$ fatty acids, sarcosinates and taurates; for example sodium lauryl sulfate, sodium coconut monoglyceride sulfonate, sodium lauryl sarcosinate, sodium lauryl isoethionate, sodium laureth carboxylate and sodium dodecylbenzenesulfonate, and mixtures thereof. Suitable nonionic surfactants include, for example, poloxamers, polyoxyethylene sorbitan esters, fatty alcohol ethoxylates, alkylphenol ethoxylates, tertiary amine oxides, tertiary phosphine oxides, dialkyl sulfoxides, and mixtures thereof. In one embodiment, the toothpaste comprises sodium lauryl sulfate, for example in an amount of from 1% to 3%, or about 2%. The toothpaste may also or alternatively contain one or more nonpolar surfactants, for example polymers and co-polymers of ethylene glycol and propylene glycol, e.g., poloxamers, i.e., nonionic triblock copolymers composed of a central hydrophobic chain of polyoxypropylene (poly(propylene oxide)) flanked by two hydrophilic chains of polyoxyethylene (poly(ethylene oxide)). The approximate lengths of the two PEG blocks is, in some embodiments, an average of about 50-150 repeat units, e.g., about 100 repeat units while the approximate length of the propylene glycol block is an average of about 25-75 repeat units, e.g., about 50-60 repeat units. In one embodiment, the poloxamer is poloxamer 407, also known by the BASF trade name Pluronic F127, e.g., in an amount of from 0.5% to 2%, for example about 1%. For example, in certain embodiments, the toothpaste compositions of the invention may contain both sodium lauryl sulfate and a poloxamer such as poloxamer 407.

The toothpaste compositions of the present invention may also contain a fluoride source—i.e., a fluoride-containing compound having a beneficial effect on the care and hygiene of the oral cavity, e.g. diminution of enamel solubility in acid and protection of the teeth against decay. Examples of suitable fluoride sources include sodium fluoride, stannous fluoride, potassium fluoride, potassium stannous fluoride (SNFZ-KF), potassium fluorozirconate, sodium hexafluorostannate, stannous chlorfluoride, and sodium monofluorophosphate (MFP). Where present, the fluoride source would provide fluoride ion in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A toothpaste for general consumer use would typically have about 1000 to about 1500 ppm, e.g., about 1100 ppm, with pediatric toothpaste having somewhat less. A dentifrice or coating for professional application could have as much as about 5,000 or even about 25,000 ppm fluoride. The amount by weight of these materials, which dissociate or release fluoride or fluorine-containing ions, will depend on the molecular weight of the counterion as well as on the particular application, but suitably may be present in an effective but non-toxic amount, usually within the range of 0.1 to 2% by weight. In some embodiments, a fluoride source selected from sodium fluoride, stannous fluoride, sodium monofluorophosphate and mixtures thereof, is used, for example the toothpaste of the invention may comprise an effective amount of sodium monofluorophosphate. In some embodiments, the fluoride source is sodium monofluorophosphate in an amount of from 0.5% to 1.0% by weight; or 0.6% to 0.9%, for example 0.7% to 0.8%, e.g., about 0.76% (about 1100 ppm fluoride ion) by weight. In some embodiments, the fluoride ion source is an effective amount of sodium fluoride, e.g., in an amount of 0.1-0.5%, e.g., about 0.24% (about 1100 ppm fluoride ion) by weight.

As will be evident to one of skill in the art, some components of the invention may perform multiple functions, and the identification of a compound as having one function herein is not meant to exclude its use for other functions in a particular composition. For example, a compound such as carboxymethylcellulose may act as a binder, but also has humectant and thickening properties.

It is also understood that compounds in formulation may naturally react, disassociate, and/or form complexes with one another. Accordingly, certain ingredients may be formed in situ (for example, it is understood that sodium chloride may be formed by reacting sodium hydroxide with hydrochloric acid), and also may in formulation exist in different forms (for example, to the extent the sodium chloride is dissolved, it will naturally disassociate into separate sodium and chloride ions, as opposed to a solid salt). As is usual in the art, the compositions of the invention are described in terms of exemplary formulation ingredients, without intending to exclude combinations of other ingredients that result in the same final compositions, or to exclude the natural reaction products of the described ingredient combinations.

In some preferred embodiments, the binder system comprises sodium calcium alginate having a sodium:calcium ratio of from 7:1 to 4:1, e.g., 6:1 to 5:1, for example about 84:16; the sodium calcium alginate binder is present in the toothpaste in an amount of 0.1%, of the toothpaste by weight; the abrasive comprises natural calcium carbonate, in an amount of from 40% to 45%; or 41% to 43%, or 42%, of the toothpaste by weight; and the toothpaste further comprises carboxymethylcellulose in an amount of from 0.1% to 2%, or 1%, of the toothpaste by weight. In some furtler embodiments, the binder system further comprises from 16% to 26% sorbitol; from 1% to 3% sodium lauryl sulfate; from 0.5% to 2% of a fluoride source; and thickener silica in an amount of 2% of the toothpaste by weight.

In some embodiments, the toothpaste further comprises one or more adjuvants selected from sweetening agents flavoring agents and coloring agents. In some embodiments, the flavoring agent is present in an amount of from 0.5% to 2.0%; or 1% of the toothpaste by weight.

In some embodiments described above, the toothpaste compositions of the invention can further include one or more sweetening agents, flavoring agents and coloring agents. Any suitable flavoring or sweetening material may be employed. Examples of suitable flavoring constituents include flavoring oils, e.g. oil of spearmint, peppermint, wintergreen, clove, sage, eucalyptus, marjoram, cinnamon, lemon, and orange, and methyl salicylate. Suitable sweetening agents include sucrose, lactose, maltose, xylitol, sodium cyclamate, perillartire, AMP (aspartyl phenyl alanine methyl ester), saccharine and the like. Suitably, flavor and sweetening agents may each or together comprise from about 0.1% to 5% more of the oral care composition. In some embodiments, the toothpaste compositions of the invention include one or more flavoring agents in an amount of from 0.5% to 2.0%; or 1%.

Various other materials may be incorporated in the oral preparations of this invention such as whitening agents, including urea peroxide, calcium peroxide, titanium dioxide, hydrogen peroxide, complexes of polyvinylpyrolidone (PVP) and hydrogen peroxide, preservatives, vitamins such as vitamin B6, B12, E and K, silicones, chlorophyll compounds, potassium salts for the treatment of dental hypersensitivity such as potassium nitrate as well as antitartar agents such as sodium tripolyphosphate and di- and tetraalkali metal pyrophosphate salts such as di- and tetrasodium pyrophosphate. These agents, when present, are incorporated in the compositions of the present invention in amounts which do not substantially adversely affect the properties and characteristics desired.

In general, each of the foregoing adjuvants may be typically incorporated in the instant toothpastes in amounts up to 5% provided they do not adversely affect the stability and cleaning properties of the non-bleeding striped dentifrice of present invention.

The invention thus provides, in one embodiment, a binder material which comprises sodium calcium alginate having a sodium:calcium ratio of from 7:1 to 4:1, e.g., 6:1 to 5:1, for example about 84:16.

The invention thus provides, in another embodiment, a toothpaste composition, for example a striped toothpaste, comprising a binder system and a calcium salt abrasive, wherein the binder comprises sodium calcium alginate having a sodium:calcium ratio of from 7:1 to 4:1, e.g., 6:1 to 5:1, for example about 84:16; for example:

1.1. Composition 1, wherein the sodium calcium alginate is present in the toothpaste in an amount of about 1%, e.g., from 0.5-1.5%, e.g., from 0.9% to 1.1%; of the toothpaste by weight.
1.2. Any foregoing composition wherein the abrasive comprises calcium carbonate, e.g., natural calcium carbonate, in an amount of from 25% to 60%; 30% to 55%; 35% to 50%; 40% to 45%; or 40%, 41%, 42%, 43%, 44% or 45% of the toothpaste by weight.
1.3. Any foregoing composition further comprising a cellulose derivative, e.g., carboxymethylcellulose (CMC), in an amount of up to 5%, or from, 0.1% to 3%; or from 0.1% to 2%, or from 0.5% to 15%, or about 1% of the toothpaste by weight.
1.4. Any foregoing composition wherein the toothpaste is free of magnesium aluminum silicate.
1.5. Any foregoing composition further comprising a humectant, which humectant comprises one or more polyols, e.g., sorbitol, in an amount of from 16% to 26%, or from 18% to 24%; about 21% of the toothpaste by weight.
1.6. Any foregoing composition further compising one or more detergents or surfactants, e.g., sodium lauryl sulfate (SLS), in an amount of from 1% to 3%, or about 2%, of the toothpaste by weight.
1.7. Any foregoing composition further comprising a fluoride source; e.g., sodium fluoride or sodium monofluorophosphate in an amount to provide about 1100 ppm fluoride ion by weight.
1.8. Any foregoing composition wherein:
the binder comprises sodium calcium alginate having a sodium:calcium ratio of flom 7:1 to 4:1, e.g., 6:1 to 5:1, for example about 84:16;
the sodium calcium alginate binder is present in the toothpaste in an amount of 0.1%, of the toothpaste by weight;
the abrasive comprises natural calcium carbonate, in an amount of from 40% to 45%; or 41% to 43%, or about 42%, of the toothpaste by weight; and
the toothpaste further comprises carboxymethylcellulose in an amount of from 0.1% to 2%, or about 1%, of the toothpaste by weight.
19. Any foregoing composition further comprising:
from 16% to 26% sorbitol;
from 1% to 3% sodium lauryl sulfate, and
from 0.5% to 2% of a fluoride source, of the toothpaste by weight.
1.10. Any foregoing composition further comprising thickener silica in an amount of from 1% to 3%; or about 2%, of the toothpaste by weight.
1.11. Any foregoing composition further comprising one or more adjuvants selected from sweetening agents flavoring agents and coloring agents.
1.12. Any foregoing composition comprising a flavoring agent in an amount of from 0.5% to 2.0%; or about 1% of the toothpaste by weight.
1.13. Any foregoing composition comprising a binder system comprising:
sodium calcium alginate having a sodium:calcium ratio of about 84:16, and which is present in the toothpaste in an amount of about 0.1%, of the toothpaste by weight;
natural calcium carbonate abrasive, in an amount of about 42%, of the toothpaste by weight;
carboxymethylcellulose in an amount of about 1%, of the toothpaste by weight;
sorbitol in an amount of about 21%, of the toothpaste by weight;
sodium lauryl sulfate in an amount of about 2%, of the toothpaste by weight;
a fluoride source, in an amount to provide about 1100 ppm by weight; and thickener silica in an amount of about 2%, of the toothpaste by weight.
1.14. Any foregoing composition, wherein the toothpaste is a striped toothpaste.

The invention further provides, in another embodiment, a method for reducing bacterial growth, cleaning the teeth, removing dental plaque, reducing dental erosion, treating dental hypersensitivity, treating gingivitis, and/or reducing tooth decay, in an oral cavity, comprising contacting the oral cavity with a toothpaste of any of Compositions 1, et seq.

The invention further provides, in another embodiment, the use of a binder comprising sodium calcium alginate having a sodium:calcium ratio of from 7:1 to 4:1, e.g., 6:1 to 5:1, for exampe about 84:16, in the manufacture of a toothpaste according to any of Compositions 1, et seq., e.g., for use in any of the methods of the preceding paragraph.

The following examples are further illustrative of the nature of the present invention, but it is understood that the invention is not limited thereto. All amounts and proportions referred to herein and in the appended claims are by weight, unless otherwise indicated.

Example 1

Viscosity Determination of SCA Formulations

The viscosity properties of formulations containing differing amounts of sodium calcium alginate (SCA) binder having a ratio of sodium alginate to calcium alginate of 84:16 was determined relative to a commercial formulation containing a natural calcium carbonate abrasive and 1% carboxymethylcellulose (CMC) and 1% magnesium aluminum silicate (MAS) as binders.

Different levels of SCA (0.2%, 0.15%, 0.11%, 0.10% and 0.09%) were used to replace MAS in the commercial formulation. The samples were monitored for 1 week for viscosity and appearance, and compared to the commercial toothpaste as a control. The results are shown in Table 1:

TABLE 1

Viscosity Determination

| Sample | Control Formula | Test Option 1 | Test Option 2 | Test Option 3 | Test Option 4 | Test Option 5 |
|---|---|---|---|---|---|---|
| CMC | 1% | 1% | 1% | 1% | 1% | 1% |
| MAS | 1% | 0 | 0 | 0 | 0 | 0 |
| SCA | 0 | 0.20% | 0.15% | 0.11% | 0.10% | 0.09% |
| Aging | Vis./×10$_4$ cps | Vis./×10$_4$ cps | Vis./×10$_4$ cps | Vis./×10$_4$ cps | Vis./×10$_4$ cps | |
| Initial | 25.7 | 33.0 | 27.8 | 26.6 | 25.2 | 21.8 |
| 1 hr | 28.7 | 38.8 | 31.2 | 30.2 | 28.8 | 25.1 |
| 2 hr | 30.9 | 43.1 | 38.5 | 34.1 | 32.1 | 28.6 |
| 3 hr | 31.2 | — | — | 34.7 | — | 31.6 |
| 1 day | 34.1 | 43.6 | 41.5 | 36.7 | 36.5 | 35.1 |
| 2 day | 36.1 | 45.4 | 44.4 | 37.5 | 37.9 | 35.4 |
| 3 day | — | — | 46.1 | 40.5 | 38.0 | — |
| 1 week | 40.6 | 48.6 | 47.8 | 43.7 | 40.5 | 38.6 |

The results show that the replacement of MAS with 0.10% by weight SCA binder provided initial and aging viscosities on parity with the commercial formulation containing MAS. In addition, the same SCA binder containing formula was also observed to have virtually identical non-dripping properties as the commercial formulation.

Example 2

Stability of Formulations

A 3-month accelerated stability test was performed on the 0.10% SCA binder containing formula compared to the commercial formula described above as a control.

The 0.10% SCA binder containing formula showed aging viscosities during the test that were at parity to the control formula.

Example 3

Rheology Test of Formulations

A rheology study was conducted on the 0.10% SCA binder containing formula compared to the commercial formula described above as a control. The results, shown in the FIGURE, show that the thixotropic properties of the two formulations are similar, and that both display an obvious thixotropy loop, indicting that both formulations are suitable for use in a striped toothpaste.

Example 4

Striping Test of Formulations

A striping study was conducted on the 0.10% SCA binder containing formula compared to the commercial formula described above as a control. The two resulting toothpastes both displayed excellent striping properties.

Example 5

Performance Test and Foaming Test of Formulations

A performance test was done 5 volunteers to evaluate the mouth feel of the 0.10% SCA binder containing formula compared to the commercial formula described above as a control. Four persons thought the SCA sample had smoother texture than the control sample; three persons thought the control sample was easier to disperse and had a more astringent feel in the mouth; and three persons thought there was no obvious difference in the paste consistency of the two samples.

Based on these result, there is no obvious difference between the two samples.

A foaming test was performed to compare the foaming effect of the 0.10% SCA binder containing formula compared to the commercial formula described above as a control. The test was done using the Ross-Miles method. The 0.10% SCA binder containing formula had a foaming power value of 142 mm, and the commercial MAS-containing formula had a foaming power value of 140 mm indicating parity of foaming power between the two formulas.

While the present invention has been described with reference to embodiments, it will be understood by those skilled in the art that various modifications and variations may be made therein without departing from the scope of the present invention as defined by the appended claims.

We claim:

1. A toothpaste comprising a binder system and a calcium salt abrasive, wherein the binder system comprises sodium calcium alginate having a sodium:calcium ratio of from 7:1 to 4:1, wherein the sodium calcium alginate is present in the toothpaste in an amount of from 0.09% to 0.1% of the toothpaste by weight, and the toothpaste further comprises carboxymethylcellulose in an amount of from 0.5% to 1.5% of the toothpaste by weight.

2. The toothpaste of claim 1, wherein the abrasive comprises calcium carbonate in an amount of from 25% to 60% of the toothpaste by weight.

3. The toothpaste of claim 1 that is free of magnesium aluminum silicate.

4. The toothpaste of claim 1 further comprising a humectant that comprises one or more polyols in an amount of from 16% to 26% of the toothpaste by weight.

5. The toothpaste of claim 1, further comprising one or more detergents or surfactants in an amount of from 1% to 3% of the toothpaste by weight.

6. The toothpaste of claim 1, further comprising a fluoride source in an amount sufficient to provide about 1100 ppm of fluoride ion by weight.

7. The toothpaste of claim 1, wherein:
the binder comprises sodium calcium alginate having a sodium:calcium ratio of from 7:1 to 4:1;
the sodium calcium alginate binder is present in the toothpaste in an amount of about 0.1%, of the toothpaste by weight;

the abrasive comprises natural calcium carbonate, in an amount of from 40% to 45%, of the toothpaste by weight; and the toothpaste further comprises carboxymethylcellulose in an amount of from 0.5% to 1.5% of the toothpaste by weight.

8. The toothpaste of claim 7, further comprising:
from 16% to 26% sorbitol;
from 1% to 3% sodium lauryl sulfate, and
from 0.5% to 2% of a fluoride source, of the toothpaste by weight.

9. The toothpaste of claim 1, further comprising thickener silica in an amount of from 1% to 3% of the toothpaste by weight.

10. The toothpaste of claim 1, further comprising one or more adjuvants selected from sweetening agents, flavoring agents and coloring agents.

11. The toothpaste of claim 1, comprising a flavoring agent in an amount of from 0.5% to 2.0% of the toothpaste by weight.

12. The toothpaste of claim 1 comprising:
a binder system comprising sodium calcium alginate having a sodium:calcium ratio of about 84:16, and which is present in the toothpaste in an amount of about 0.1%, of the toothpaste by weight;
natural calcium carbonate abrasive, in an amount of about 42%, of the toothpaste by weight;
carboxymethylcellulose in an amount of about 1%, of the toothpaste by weight;
sorbitol in an amount of about 21% of the toothpaste by weight;
sodium lauryl sulfate in an amount of about 2%, of the toothpaste by weight;
a fluoride source, in an amount to provide about 1100 ppm fluoride ion by weight; and thickener silica in an amount of about 2% of the toothpaste by weight.

13. The toothpaste of claim 1, wherein the toothpaste is a striped toothpaste.

14. A method for reducing bacterial growth, cleaning the teeth, removing dental plaque, reducing dental erosion, treating dental hypersensitivity, treating gingivitis, and/or reducing tooth decay in an oral cavity, comprising contacting the oral cavity with a toothpaste of claim 1.

15. The toothpaste of claim 4 wherein the one or more polyols comprise sorbitol.

16. A toothpaste comprising a binder system and an calcium salt abrasive, wherein the binder system comprises sodium calcium alginate having a sodium:calcium ratio of from 7:1 to 4:1, wherein the sodium calcium alginate is present in the toothpaste in an amount of about 0.1% of the toothpaste by weight, and the toothpaste further comprises carboxymethylcellulose in an amount of from 0.5% to 1.5% of the toothpaste by weight.

* * * * *